(12) United States Patent
Silk et al.

(10) Patent No.: US 9,598,674 B2
(45) Date of Patent: Mar. 21, 2017

(54) DENDRITIC CELLS OBTAINED FROM INDUCED PLURIPOTENT STEM CELLS (IPSCS)

(75) Inventors: Kathryn Silk, Oxford (GB); Paul Fairchild, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 147 days.

(21) Appl. No.: 14/002,096

(22) PCT Filed: Feb. 28, 2012

(86) PCT No.: PCT/GB2012/050447
§ 371 (c)(1),
(2), (4) Date: Oct. 30, 2013

(87) PCT Pub. No.: WO2012/127206
PCT Pub. Date: Sep. 27, 2012

(65) Prior Publication Data
US 2014/0050762 A1    Feb. 20, 2014

(30) Foreign Application Priority Data

Mar. 1, 2011    (GB) .................................. 1103600.1

(51) Int. Cl.
*C12N 5/00*    (2006.01)
*C12N 5/02*    (2006.01)
*C12N 5/0784*    (2010.01)

(52) U.S. Cl.
CPC ........ *C12N 5/0639* (2013.01); *C12N 2501/02* (2013.01); *C12N 2501/125* (2013.01); *C12N 2501/155* (2013.01); *C12N 2501/165* (2013.01); *C12N 2501/22* (2013.01); *C12N 2501/2301* (2013.01); *C12N 2501/2304* (2013.01); *C12N 2501/24* (2013.01); *C12N 2501/25* (2013.01); *C12N 2506/45* (2013.01)

(58) Field of Classification Search
None
See application file for complete search history.

(56) References Cited

U.S. PATENT DOCUMENTS

2010/0081199 A1    4/2010    Slukvin et al.

FOREIGN PATENT DOCUMENTS

WO    2007069666 A1    6/2007
WO    2010099539 A1    9/2010

OTHER PUBLICATIONS

Hoffmann et al., 2000, Can. Res. vol. 60: 3542-3549.*
Hoene et al., 2006, J. Leuk. Biol. vol. 80: 1328-36.*
Hoeffel et al., 2007, Immunity, vol. 27: 481-492.*
Mittag et al., 2011, J. Immunol. vol. 186: 6207-17.*
Franco et al., 2008, Gen. Vacc. Ther. vol. 6: 1-11.*
Akira et al., "Pathogen Recognition and Innate Immunity", Cell, 124:783-801, 2006.
Bachem et al., "Superior antigen cross-presentation and XCR1 expression define human CD11c+CD141+ cells as homologues of mouse CD8+ dendritic cells", JEM, 207(6):1273-1281, 2010.
Carpenter et al., "Human induced pluripotent stem cells are capable of B-cell lymphopoiesis", Blood, 117:4008-4011, 2011.
Choi et al., "Generation of mature human myelomonocytic cells through expansion and differentiation of pluripotent stem cell-derived lin-CD34+CD43+CD45+ progenitors", J. Clin. Invest., 119(9):2818-2829, 2009.
Corzat et al., "The XC chemokine receptor 1 is a conserved selective marker of mammalian cells homologous to mouse CD8a+ dendritic cells", JEM, 207(6):1283-1292, 2010.
Dorner et al., "Selective Expression of the Chemokine Receptor XCR1 on Cross-presenting Dendritic Cells Determines Cooperation with CD8+ T Cells", Immunity, 31:823-833, 2009.
Edwards et al., "Toll-like receptor expression in murine DC subsets: lack of TLR7 expression by CD8a+ DC correlates with unresponsiveness to imidazoquinolines", Eur. J. Immunol, 33:827-833, 2003.
Engell-Noerregaard et al., "Review of clinical studies on dendritic cell-based vaccination of patients with malignant melanoma: assessment of correlation between clinical response and vaccine parameters", Cancer Immunol Immunother, 58:1-14, 2009.
Fukuma et al., "Cancer prevention with semi-allogeneic ES cell-derived dendritic cells", Biochem. and Biophys. Research Comm., 335:5-13, 2005.
Fukushima et al., "Multiple Antigen-targeted Immunotherapy With a-Galactosylceramide-loaded and Genetically Engineered Dendritic Cells Derived From Embryonic Stem Cells", J. Immunother., 32:219-231, 2009.
Gallois & Bhardwaj, "A needle in the 'cancer vaccine' haystack", Nature Medicine, 16(8):854-856, 2010.
Hanna et al., "Somatic cell reprogramming and transitons between pluripotent states: facts, hypotheses, unresolved issues", Cell, 143(4):508-525, 2010.
Hirata et al., "Prevention of Experimental Autoimmune Encephalomyelitis by Transfer of Embryonic Stem Cell-Derived Dendritic Cells Expressing Myelin Oligodendrocyte Glycoprotein Peptide along with TRAIL or Programmed Death-1 Ligand1", J. Immunology, 174:1888-1897, 2005.
Jarrossay et al., "Specialization and complementaity in microbial molecule recognition by human myeloid and plasmacytoid dendritic cells", Eur. J. Immunol., 31:3388-3393, 2001.
Jongbloed et al., "Human CD141+ (BDCA-3)+ dendritic cells (DCs) represent a unique myeloid DC subset that cross-presents necrotic cell antigens", JEM, 207(6):1247-1260, 2010.
Lin et al., "Development of Feeder-Free Culture Systems for Generation of ckit+sca1+ Progenitors from Mouse iPS Cells", Stem Cell Rev., 7(3):736-747, 2011.
Muzio et al., "Differential Expression and Regulation of Toll-Like Receptors (TLR) in Human Leukocytes: Selective Expression of TLR3 in Dendritic Cells", J. Immunology, 164:5998-6004, 2000.

(Continued)

*Primary Examiner* — Amy Juedes
(74) *Attorney, Agent, or Firm* — Norton Rose Fulbright US LLP (57) ABSTRACT

The invention relates to dendritic cells produced from human induced pluripotent stems cells (iPSC). The invention also relates to methods for making and methods of using the dendritic cells of the invention.

9 Claims, 6 Drawing Sheets

(56) References Cited

OTHER PUBLICATIONS

Paluka et al., "Designing vaccines based on biology of human dendritic cell subsets", Immunity, 33(4):646-478, 2010.
Poulin et al., "Characterization of human DNGR-1+ BDCA3+ leukocytes as putative equivalents of mouse CD8a+ dendritic cells", JEM, 207(6):1261-1271, 2010.
Robsen et al., "Presentation of tumour antigens by dendritic cells and challenges faced", Curr. Opin. Immunol., 22:137-144, 2010.
Senju et al., "Characterization of Dendritic Cells and Macrophages Generated by Directed Differentiation from Mouse Induced Pluripotent Stem Cells", Stem Cells, 27:1021-1031, 2009.
Senju et al., "Pluripotent stem cell-derived dendritic cells for immunotherapy", Frontiers in Bioscience, E2:1520-1527, 2010.
Senju et al., "Pluripotent stem cells as source of dendritic cells for immune therapy", Int. J. Hematol, 91:392-400, 2010.
Senju et al., "Generation of dendritic cells and macrophages from human induced pluripotent stem cells aiming at cell therapy", Gene Therapy, 18:874-883, 2011.
Senju et al., "Immunotherapy with pluripotent stem cell-derived dendritic cells", Semin Immunopathol, 33:603-612, 2011.
Silk et al., "Cross-presentation of tumour antigens by human induced pluripotent stem cell-dereived CD141+XCR1+ dendritic cells", Gene Therapy, 19:1035-1040, 2012.
Stadtfeld & Hochedlinger, "Induced pluripotency: history, mechanisms, and applications", Genes Dev., 24:2239-2263, 2010.
Su et al., "Differentiation of Human Embryonic Stem Cells into Immunostimulatory Dendritic Cells under Feeder-Free Culture Conditions", Clin. Cancer Res., 14(19):6207-6217, 2008.
Tseng et al., "Generation of immunogenic dendritic cells from human embyonic stem cells without serum and feeder cells", Regen. Med., 4(4):513-526, 2009.
Silk, KM., et al; Cross-Presentation of Tumour Antigens by Human Induced Pluripotent Stem Cell-Derived CD141+ XCR1+ Dendritic Cells; Gene Therapy (2012); 19, 1035-1040; Macmillian Publishers Ltd.
Kadowaki, Norimitsu, et al.; Subsets of Human Dendritic Cell Precursors Express Different Toll-like Receptors and Respond to Different Microbioal Antigens; (2001) J. Exp. Med. 863-869.
Bauer, Marc, et al; Bacterial CpG-DNA Triggers Activation and Maturation of Human CD11c-,CD123+ Dendritic Cells; (2001) J. Immunol. 166: P5000-5007.
Krug, Anne; et al; Toll-like Receptor Expression Reveals CpG DNA as a Unique Microbial Stimulus for Plasmacytoid Dendritic Cells which Synergizes with CD40 Ligand to Induce High Amounts of IL-12; (2001)Eur. J. Immunol. 31: 3026-3037.
Hartmann, G.; et al; CpG DNA: A Potent Signal for Growth, Activation, and Maturation of Human Dentritic Cells; (1999); PNSA 96: P9305-9310.
Jarrossay, David; Specialization and Complementarity in Microbial Molecule Recognition by Human Myeloid and Plasmacytoid Dendritic Cells; (2001); Eur. J. Immunol. 3388-3393.
Pulendran, "Modulating vaccine responses with dendritic cells and Toll-like receptors", Immunological Reviews, 2004, vol. 199, pp. 227-250.
Schulz et al., "Toll-like receptor 3 promotes cross-priming to virus-infected cells", Nature, vol. 433, Feb. 24, 2005, pp. 887-892.

* cited by examiner

DENDRITIC CELLS OBTAINED FROM INDUCED PLURIPOTENT STEM CELLS (IPSCS)

This Application claims priority to PCT Patent Application Serial No. PCT/GB2012/050447 filed on Feb. 28, 2012, which claims priority to GB Patent Application Serial No. 1103600.1 filed on Mar. 1, 2011, both of which applications are incorporated by reference herein in their entirety.

FIELD OF THE INVENTION

The invention relates to dendritic cells (DCs) produced from human induced pluripotent stems cells (iPSCs). The invention also relates to methods for making and methods of using the DCs of the invention.

BACKGROUND TO THE INVENTION

The use of dendritic cells (DCs) to prime responses to tumor-associated antigens (TAAs) provides a promising approach to cancer immunotherapy (Palucka et al., *Immunity* 33, 464-478 (2010)), but clinically-relevant responses have frequently been disappointing (Engell-Noerregaard et al., *Cancer Immunol. Immunother.* 58, 1-14 (2009); and Robson et al., *Curr. Opin. Immunol.* 22, 137-144 (2010)). This is partly due to the properties of the DCs most commonly used. Currently, autologous DC, differentiated in vitro from the patient's own peripheral blood monocytes, remain the preferred source of cells for cancer immunotherapy. These monocyte-derived DCs (MoDCs) show significant donor-to-donor variation, which is frequently compounded by the side-effects of chemotherapy. Furthermore, moDCs display a limited capacity for cross-priming of antigen specific $CD8^+$ cytotoxic T lymphocytes (CTLs), creating a dependence on the use of exogenous peptides derived from TAAs and further restricting the scope of such an approach to those HLA haplotypes for which the immunodominant epitopes are known. Since $CD8\alpha^+$ DC in mice are peculiarly capable of cross-presentation, the recent identification of $CD141^+$ $XCR1^+$ DC as their functional equivalent in humans (Bachem et al., *J. Exp. Med.* 207, 1273-1281 (2010); and Crozat et al., *J. Exp. Med.* 207, 1283-1292 (2010)) has suggested that this subset may be better suited to the induction of anti-tumor responses (Gallois & Bhardwaj, *Nature Med.* 16, 854-856 (2010)). However, such cells are only present in trace numbers in peripheral blood and low yields are obtained following the culture of progenitors from cord blood (Poulin et al., *J. Exp. Med.* 207, 1261-1271 (2010)). As a result, they do not represent a feasible treatment for cancer.

SUMMARY OF THE INVENTION

The inventors have surprisingly demonstrated that large numbers of dendritic cells (DCs) capable of cross presenting antigens to naïve cytotoxic T lymphocytes (CTLs) can be produced from human induced pluripotent stem cells (iPSCs). The invention therefore provides a dendritic cell produced from a human induced pluripotent stem cell (iPSC), wherein the dendritic cell is capable of cross presenting an antigen to naïve $CD8^+$ T lymphocytes.

The invention also provides:
- a population comprising two or more dendritic cells of the invention;
- a population comprising more than $5.1 \times 10^5$ dendritic cells of the invention;
- a pharmaceutical composition comprising (a) a dendritic cell of the invention or a population of the invention and (b) a pharmaceutically acceptable carrier or diluent;
- a method of producing a population of dendritic cells of the invention, comprising culturing human iPSCs under conditions which induce the iPSCs to differentiate into dendritic cells;
- a method of inducing a CTL response to an antigen in a patient in need thereof, comprising administering to the patient an immunologically effective number of dendritic cells of the invention which are loaded or transfected with the antigen and thereby inducing a CTL response to the antigen in the patient; and
- a method of inducing tolerance to an antigen in a patient in need thereof, comprising administering to the patient an immunologically effective number of immature dendritic cells produced using the method of the invention or dendritic cells of the invention which have been treated to render then tolerogenic and thereby inducing tolerance to the antigen in the patient, wherein the DCs are loaded or transfected with the antigen.

BRIEF DESCRIPTION OF THE FIGURES

FIG. 1 shows the pluripotency of the C19 hiPSC line. (a) Phase contrast micrograph of an hiPSC colony, the individual cells of which display a prominent nucleus, similar to hESC and other hiPSC lines. Scale bar: 40 µm. (b) C19 cells were stained for the surface markers SSEA-4 and TRA1-60 and for the transcription factors Oct-4 and Nanog, known to play an important role in conferring pluripotency. Viable cells were analysed by using 7-AAD to exclude dead cells. (c) C19 hiPSC have the capacity to differentiate into cell types derived from each of the three embryonic germ layers. Embryoid bodies (EB) were generated by culturing clusters of hiPSC in suspension for 4-12 days before being plated onto tissue culture plastic for a further 14-19 days to promote their spontaneous differentiation. Cultures were fixed at room temperature for 20 min in 4% paraformaldehyde (v/v), washed and stained with antibodies against SOX17 conjugated to NorthernLights-557 (polyclonal goat IgG; R&D Systems), CD34 (clone AC136; Miltenyi Biotec), βIII tubulin (clone SDL.3D10; Sigma-Aldrich Ltd) and appropriate Alexa-conjugated secondary antibodies (Invitrogen Ltd.) according to the manufacturer's instructions. SOX17 is a transcription factor important in the development of endoderm, CD34 is expressed by haematopoietic and endothelial progenitor cells of mesodermal origin and βIII-tubulin stains neurons that are ectodermally-derived. Scale bar: 100 µm.

FIG. 2 shows the characterisation of DC differentiated from hiPSC. (a) Phase contrast micrograph showing a cluster of ipDC and the morphology of individual cells (inset). Scale bar: 40 µm. (b) Expression of DC-associated markers by ipDC (blue histograms) compared to isotype matched controls (red histograms). (c) Comparison of the phenotype of ipDC and moDC following maturation with a cytokine cocktail. DC were gated as the $CD11c^{hi}$ population and dead cells excluded using 7-AAD. (d) ipDC stimulate proliferative responses among naïve allogeneic T cells. DC were mitomycin C (MMC) treated, washed and titrated into cultures of PBL from an allogeneic donor at a top stimulator:responder ratio of 1:10. Wells were pulsed with $^3$H-thymidine on day 4 and harvested 18 h later. Values of cpm represent the average of triplicate cultures±S.D. Data are representative of 3 independent experiments.

FIG. 3 shows cross-presentation of TAA by ipDC. (a) Cultures of ipDC, but not moDC, contain cells co-expressing CD141 and XCR1. DC were gated on the CD11c$^{hi}$ population. (b) Top panel: (i) 0 nM Melan A$_{26-35}$ peptide, (ii) 10 nM Melan A$_{26-35}$ peptide and (iii) 1000 nM Melan A$_{26-35}$ peptide. Bottom panel: (i) fixed without Melan A$_{26-35}$ peptide, (ii) fixed with Melan A$_{26-35}$ peptide and (iii) live with Melan A$_{26-35}$ peptide. Whereas both HLA-A*0201$^+$ ipDC and moDC pulsed with the Melan A$_{26-35}$ peptide elicited IFN-γ production from the CD8$^+$ T cell clone 2D10 (top panel), when incubated with 1 μM Melan A protein, only ipDC were able to cross-present the epitope to 2D10 (bottom panel). Bars represent the mean of replicate cultures±S.D. Data are representative of 3 independent experiments. (c) ipDC are able to cross-prime naïve Melan A-specific T cells from an HLA-A*0201$^+$ donor. T cells were co-stained on d14 for CD8 and the relevant TCR using a HLA-A*0201-Melan A$_{26-35}$ tetramer. Data are representative of 3 independent experiments. (d) Priming of CD8$^+$ T cells by ipDC elicits IFN-γ production. Following in vitro culture of naïve T cells with either unpulsed or Melan A$_{26-35}$ pulsed DC, cells were re-stimulated with tetramer and peptide and stained for surface CD8 and intracellular IFN-γ. Dead cells were excluded using 7-AAD.

FIG. 5 shows naïve tumor-specific CTL primed by ipDC express perforin. DC were either pulsed with Melan A$_{26-35}$ peptide or left unpulsed and cultured with naïve T cells for 14 days. T cells were restimulated with tetramer and peptide followed by CD8 surface staining and intracellular staining for perforin expression. Dead cells were excluded from the analysis using 7-AAD.

DETAILED DESCRIPTION OF THE INVENTION

It is to be understood that different applications of the disclosed methods may be tailored to the specific needs in the art. It is also to be understood that the terminology used herein is for the purpose of describing particular embodiments of the invention only, and is not intended to be limiting.

In addition, as used in this specification and the appended claims, the singular forms "a", "an", and "the" include plural referents unless the content clearly dictates otherwise. Thus, for example, reference to "a cell" includes "cells", reference to "an antigen" includes two or more such antigens, reference to "a patient" includes two or more such patients, and the like.

All publications, patents and patent applications cited herein, whether supra or infra, are hereby incorporated by reference in their entirety.

DCs of the Invention

The present invention provides a dendritic cell (DC) produced from a human induced pluripotent stem cell (iPSC), wherein the DC is capable of cross presenting an antigen to naïve CD8$^+$ T lymphocytes. The DCs of the invention have numerous advantages. The key advantages will be summarized here. However, further advantages will become apparent from the discussion below.

The DCs of the invention may advantageously be used to induce CTL responses to a particular antigen in a human patient. The DCs may therefore be used for the effective treatment of a variety of diseases in which CTL responses are preferred, such as cancer or infections by a pathogen.

As discussed in more detail below, human iPSCs are produced from somatic cells, such as dermal fibroblasts, taken from a human individual. Since the DCs are produced from iPSCs, they may be autologous for the patient to be treated and thereby avoid the risk of immunological rejection by the patient. The immunological response to the antigen in the patient is also improved relative to non-autologous DCs.

It is possible, in principle, to produce an unlimited number of iPSCs from a single individual, since iPSC are capable of indefinite self-renewal. It is certainly possible to produce very large numbers of iPSCs from a single individual. The DCs of the invention can therefore be made in large numbers. It is advantageously possible to provide many more antigen cross-presenting DCs using the invention than by isolating the relevant cells from the peripheral blood of a patient. This is explained in more detail below.

iPSCs can be maintained in culture indefinitely as a renewable bank from which DCs of the invention can be produced. Numerous populations of the DCs of the invention can be made from one population of iPSCs. This facilitates repeated treatment of the patient without the need to take numerous samples of peripheral blood.

The DCs of the invention are produced in clinically relevant conditions, for instance in the absence of trace amounts of endotoxins and other environmental contaminants, as well as animal products such as fetal calf serum. This makes the DCs of the invention particularly suitable for administration to patients.

Since the DCs of the invention are produced from iPSCs, they are substantially homologous and may be autologous. They also avoid donor-to-donor variation, which frequently occurs with monocyte-derived DCs (moDCs). Numerous populations of DCs of the invention can be produced from a single sample take from the patient before any other cancer therapy, such as chemotherapy or radiotherapy, has begun. Therefore, the DCs of the invention can avoid any of the detrimental effects of those treatments. However, even if the DCs are derived from a sample taken after cancer therapy has begun, they are still largely unaffected because the cells (e.g. skin cells) from which they are ultimately derived are in general not affected by such therapy.

The DCs of the invention can also be made much more quickly than DCs from other populations of pluripotent cells, such as human embryonic stem cells (hESCs). DCs can be produced from iPSCs in less than 30 days, rather than the 30 to 40 days it takes to produce DCs from hESCs.

The production of DCs from iPSCs avoids the moral and ethical implications involved with using other types of stem cells, such human embryonic stem cells (hESCs).

As discussed in more detail below, the DCs of the invention are surprisingly responsive to ligands of various Toll-like receptors (TLRs), especially TLR2, TLR3, TLR4, TLR7 and TLR9, and so their ability to cross present antigens in vivo may be fine-tuned.

The DCs of the invention are produced from human iPSCs. The DCs of the invention are therefore human.

DCs have different stages in their development during which they, for example, predominately take up antigen, rather than present it. For example, it is thought that DCs may have immature stages characterised by the uptake of large amounts of potential antigens and more mature stages characterised by lower amounts of antigen uptake, but increased amounts of antigen presentation of the antigens they acquired previously. The DCs of the invention are initially immature but may be induced to mature as evidenced by their ability to cross present antigen to naïve or memory CD8$^+$ T cells. Methods for making mature DCs are disclosed in more detail below. The DCs may of course be manipulated in vitro and this may allow control of whether the cells are exposed to stimuli which promote dendritic cell maturation. Thus, by ensuring that the cells are exposed to stimuli responsible for inducing maturation, the resultant cells may be used to promote an immune response when they are transferred to a patient.

The DCs of the invention can be identified as dendritic cells using standard methods known in the art, including expression of lineage restricted markers, structural and functional characteristics. The DCs will express detectable levels of cell surface markers known to be characteristic of dendritic cells. In particular the DCs may express detectable levels of any one of CD11c, CD209 (also known as DC sign), CD13, low levels of CD200R, CD11b, CD83 and CD40. The cells may be CD14$^{lo}$. In some cases the cells may express all of CD11c, CD209 and CD13 and may also be CD14$^{lo}$.

The DCs of the invention typically express MHC molecules. The DCs of the invention typically express both MHC class I and MHC class II. The DCs of the invention preferably express detectable levels of MHC class II. Any of the HLA haplotypes may be present on the DCs of the invention.

In response to a maturation cocktail, such an one comprising tumor necrosis factor-α (TNFα), prostaglandin-E$_2$ (PGE$_2$), interleukin-1β (IL-1β) and interferon-γ (IFNγ), the DCs of the invention will secrete high concentrations of the pro-inflammatory cytokine IL-6.

Morphologically, DCs are typically characterised by extensive veils of cytoplasm and individual cells with many dendrites. Another defining characteristic of DCs is their ability to stimulate an allogeneic T cell response in a mixed leukocyte reaction (MLR). In an MLR, DCs are cultured together with allogeneic lymphocytes. Due to the histocompatibility mismatch between the cells, T cells recognise allogeneic MHC molecules expressed by DC as foreign and respond by proliferating vigorously in culture.

The DCs of the invention are distinguished from known DCs, such as moDCs, in various ways. The DCs of the invention preferably express detectable levels of XCR1. This cell surface antigen is typically expressed by cells capable of antigen cross presentation.

The DCs of the invention lack significant expression of the plasmacytoid DC markers CD123 and BDCA-2. They also display a CD11b$^{lo}$CD141$^{hi}$ phenotype.

The DCs of the invention preferably either express detectable levels of certain Toll-like receptors (TLRs) or respond to ligands of particular TLRs. TLRs are pattern recognition receptors that bind to moieties that are conserved amongst microbes known as pathogen associated molecular patterns (PAMPs). Binding of TLR ligands to TLRs initiates signalling cascades inside DCs that result in the production of inflammatory mediators and up-regulation of co-stimulatory molecules important in initiating immune responses. The ability of the DCs of the invention to respond to various TLR ligands is advantageous because it allows the ability of the DCs to cross present antigen to naïve CD8$^+$ T cells in vivo to be improved by ligands of TLRs.

The DCs of the invention preferably express detectable levels of TLR9. TLR9 recognizes unmethylated 2'-deoxyribo(cytidine-phospho-guanosine) (CpG) DNA motifs that are frequently present in bacteria and viruses, but are rare in mammalian cells. Since the DCs of the invention express TLR9, they are capable of recognising CpG DNA motifs. The DCs of the invention may be used to treat bacterial or viral infections. The therapeutic methods of the invention may also involve combined therapy with DCs of the invention and one or more CpG motifs. CD141$^+$XCR1$^+$ DCs isolated from human peripheral blood do not express detectable levels of TLR9 (Bachem et al., *J. Exp. Med.* 207, 1273-1281 (2010); and Crozat et al., *J. Exp. Med.* 207, 1283-1292 (2010)).

The DCs of the invention preferably express detectable levels of TLR3. TLR3 was originally identified as recognizing a synthetic analog of double-stranded RNA (dsRNA), namely polyinosinic-polycytidylic acid (poly(I:C)), which mimics viral infection and induces antiviral immune responses by promoting the production of both type I interferon and inflammatory cytokines (Choe et al., Science 309, 581-585 (2005)). The DCs of the invention may be used to treat viral infections. The therapeutic methods of the invention may involve combined therapy with DCs of the invention and one or more poly(I:C)s.

The DCs of the invention preferably express detectable levels of TLR7. TLR7 recognises RNA viruses in a replication-independent manner.

The DCs of invention preferably express low levels of TLR2 and TLR4 when determined by flow cytometry. In any case, the DCs of the invention preferably respond to ligands of TLR2 and TLR4 in functional assays, such as the secretion of IL-6, detected by ELISA assays. TLR-2 (also known as CD282) is a surface membrane receptor protein which plays a fundamental role in pathogen recognition and activation of innate immunity. This protein is expressed most abundantly in peripheral blood leukocytes, and mediates host response to Gram-positive bacteria and yeast via stimulation of NF-κB. TLR2 is involved in the recognition of a wide range of PAMPs derived from bacteria, fungi, parasites and viruses (Akira, et al., Cell 124, 783-801 (2006)). These include lipopeptides from bacteria, peptidoglycan and lipoteichoic acid from Gram-positive bacteria, lipoarabinomannan from mycobacteria, zymosan from fungi, tGPI-mucin from *Trypanosoma cruzi* and the hemagglutinin protein from measles virus. TLR2 generally forms heterodimers with TLR1 or TLR6. Specifically, the TLR2-TLR1 heterodimer recognizes triacylated lipopeptides from Gram-negative bacteria and mycoplasma, whereas the TLR2-TLR6 heterodimer recognizes diacylated lipopeptides from Gram positive bacteria and mycoplasma. The DCs of the invention may be used to treat chronic infections by bacteria, fungi, parasites and viruses. The therapeutic methods of the invention may involve combined therapy with DCs of the invention and one or more lipopeptide, peptidoglycan, lipoteichoic acid, lipoarabinomannan, zymosan, tGPI-mucin and hemagglutinin protein.

TLR4 (also known as CD284; Akira, et al., Cell 124, 783-801 (2006)) is a cell surface protein that detects lipopolysaccharide on Gram-negative bacteria and is thus important in the activation of the innate immune system. The DCs of the invention may be used to treat Gram-negative bacterial infections. The therapeutic methods of the invention may involve combined therapy with DCs of the invention and one or more bacterial lipopolysaccharides.

Standard methods known in the art may be used to determine the detectable expression, low expression or lack thereof of the various markers discussed above. Suitable methods include, but are not limited to, immunocytochemistry, flow cytometry and quantitative PCR. DC responses to TLR ligands may also be measured using standard assays known in the art. Suitable methods include, but are not limited to, enzyme-linked immunosorbent assays (ELISA) for the secretion of cytokines, enhanced mixed leukocyte reactions and up-regulation of co-stimulatory molecules and maturation markers, measured by flow cytometry. Specific methods that may be used are disclosed in the Example.

The DCs of the invention are capable of cross presenting antigen to naïve $CD8^+$ T cells. The classical pathways of antigen processing and presentation in DCs are the exogenous pathway (involving MHC class II) and the endogenous pathway (dependent on MHC class I). $CD4^+$ T lymphocyte responses are directed by antigen presentation on MHC class II molecules, whereas $CD8^+$ CTL responses are directed by antigen presentation on MHC class I molecules. DCs are capable of taking up exogenous antigen, processing it and presenting the resulting peptides on their cell surfaces via MHC class II molecules to stimulate $CD4^+$ T lymphocyte responses. Endogenous antigens that may be derived from the DCs themselves, or from intracellular pathogens such as viruses, are processed and presented on the surfaces of the DCs via MHC class I molecules to stimulate $CD8^+$ CTLs.

$CD8^+$ CTL responses are particularly important in antiviral and anti-tumor immunity because the CTL cells are capable of killing the infected or tumor cells. However, using the classical endogenous pathway of antigen presentation, DCs will only activate CTL-based responses if they themselves become infected with the incriminating viral pathogen or become transformed. Many DCs, including moDC, have very limited capacity to process and present exogenous antigens via MHC class I and thereby stimulate anti-tumor or anti-viral CTL responses.

Cross-presentation is a phenomenon whereby a limited subset of DCs is capable of taking up, processing and presenting exogenous antigen on MHC class I and thereby stimulating CTL responses. In this context, "exogenous" antigen particularly includes proteins, polypeptides or peptides (e.g. synthetic polypeptides and peptides) which are not derived from the DCs themselves. The DCs of the invention are capable of cross presenting antigen to naïve $CD8^+$ T cells. The DCs of the invention are therefore capable of taking up, processing and presenting exogenous antigen via MHC class I molecules. The cells may, therefore, be loaded or transfected with a tumor-derived or pathogen-derived antigen and used in vivo to induce CTL responses against the tumor or pathogen. This is discussed in more detail below.

The antigen, or peptides derived from it, will be presented via MHC I. In some instances, the antigen may be presented by both MHC class I and MHC class II.

The ability of the DCs of the invention to cross-present antigen may be tested using any assay known in the art. The DCs of the invention may be loaded or transfected with the antigen as discussed in more detail below. The DCs of the invention are typically loaded with or cultured in the presence of a test antigen and the ability of the cells to present a peptide derived from the test antigen using MHC class I molecules is determined Presentation may be measured by culturing the cross-presenting DCs with appropriate $CD8^+$ HLA-restricted T lymphocytes which have been primed with the antigen in question and determining whether or not such T lymphocytes produce IFN-γ. Alternatively, well-characterised MHC class I-restricted T cell clones of known antigen specificity may be used as a readout for cross-presentation of whole exogenous antigen. A specific assay is disclosed in the Example.

A DC of the invention may be isolated, substantially isolated, purified or substantially purified. The DC is isolated or purified if it is completely free of any other components, such as culture medium, other cells of the invention or other cell types. The DC is substantially isolated if it is mixed with carriers or diluents, such as culture medium, which will not interfere with its intended use. Alternatively, the DC of the invention may be present in a growth matrix or immobilized on a surface as discussed below.

DCs of the invention may be isolated using a variety of techniques including antibody-based techniques. Cells may be isolated using negative and positive selection techniques based on the binding of monoclonal antibodies to those surface markers which are present on the DC. Hence, the DCs may be separated using any antibody-based technique, including FACS and magnetic bead separation.

As discussed in more detail below, the DCs may be treated ex vivo. Thus the cells may be loaded or transfected with antigen and then used therapeutically in the methods of the invention. The invention therefore provides a DC of the invention loaded or transfected with an antigen. Suitable antigens are discussed below. The invention further provides a DC of the invention which comprises a nucleic acid encoding an antigen. The invention also provides a DC of the invention which has been infected by a virus particle or another vector capable of expressing an antigen.

Population of the Invention

The invention also provides a population of two or more DC cells of the invention. Any number of cells may be present in the population.

In a preferred embodiment of the invention, the population comprises more cross-presenting DCs than can be obtained from one unit of human peripheral blood. The number of peripheral blood mononuclear cells (PBMCs) obtained from the peripheral blood of an adult human is $2$-$3 \times 10^6$/ml. The maximum volume of blood that can be taken from a human being for donation is 568 ml (1 pint). Therefore, the number of PBMCs in a unit of donated blood is $1.14$-$1.7 \times 10^9$. The percentage of $CD141^+$ DCs in human PBMCs is ~0.03% (Jongbloed, S. L. et al. *J. Exp. Med.* 207, 1247-1260 (2010)). Therefore, the total number of $CD141^+$ DCs that can be obtained from a unit of donated blood is $3.4$-$5.1 \times 10^5$. Hence, in a preferred embodiment, the population of the invention comprises more than $5.1 \times 10^5$ DCs of the invention. The population more preferably comprises at least $5.2 \times 10^5$, at least $5.5 \times 10^5$, at least $6.0 \times 10^5$, at least $6.5 \times 10^5$, at least $7.0 \times 10^5$, at least $7.5 \times 10^5$, at least $8.0 \times 10^5$, at least $8.5 \times 10^5$, at least $9.0 \times 10^5$, at least $9.5 \times 10^5$ or at least $1.0 \times 10^6$ DCs of the invention. In some instance, the population may comprise at least $1.0 \times 10^7$, at least $1.0 \times 10^8$, at least $1.0 \times 10^9$, at least $1.0 \times 10^{10}$, at least $1.0 \times 10^{11}$ or at least $1.0 \times 10^{12}$ DCs of the invention.

Such numbers can be achieved using the invention. For instance, using the method of the invention described below, an average yield of non-adherent cells following differentiation is ~$2 \times 10^5$ cells/well. The average percentage of DCs of the invention (defined $CD11c^{hi}CD141^+XCR1^+$) is 9.26%-

37.6%. Therefore, the number of DCs of the invention is 1.1-4.5×10$^4$ per well. This equates to 6.6×10$^4$-2.7×10$^5$/plate or 6.6×10$^5$-2.7×10$^6$/10 plates. As a result, any number of DCs of the invention may be generated by scaling up the number of culture plates used in the method. The scalability of the method is merely dependent on the number of human iPSCs that may be obtained. That number is virtually unlimited. Methods for obtaining iPSCs from humans are discussed in more detail below.

The populations of the invention are advantageous for therapy as discussed below. This ability to produce populations comprising large numbers of cross presenting DCs is one of the key advantages of the invention. The invention allows the generation of sustainable populations of DCs in sufficient numbers to allow several cycles of effective therapy in a patient.

The population of the invention is preferably homologous. In other words, all of the DCs in the population are preferably genotypically and phenotypically identical. The population is preferably autologous. However, the population can also be semi-allogeneic. Semi-allogeneic populations are typically produced from the differentiation of partially-matched, clinically-approved iPSC lines, obtained from a public bank. In other words, all of the cells in the population are preferably genetically identical or sufficiently genetically identical that the population is immunologically compatible with a patient into which the population will be administered. Since the DCs of the invention may be derived from a patient via iPSCs, they may be autologous with the patient to be treated (i.e. genetically identical with the patient or sufficiently genetically identical that they are compatible for administration to the patient).

The population of the invention may be isolated, substantially isolated, purified or substantially purified. A population is isolated or purified if it is completely free of any other components, such as culture medium and other cells. A population is substantially isolated if it is mixed with carriers or diluents, such as culture medium, which will not interfere with its intended use. Other carriers and diluents are discussed in more detail below. A substantially isolated or substantially purified population does not comprise cells other than the DCs of the invention. In some embodiments, the population of the invention may be present in a growth matrix or immobilized on a surface as discussed below.

The population is typically cultured in vitro. Techniques for culturing cells are well known to a person skilled in the art. The cells are typically cultured under standard conditions of 37° C., 5% CO$_2$ in medium without serum. The cells may be cultured in any suitable flask or vessel, including wells of a flat plate such as a standard 6 well plate. Such plates are commercially available from Fisher scientific, VWR suppliers, Nunc, Starstedt or Falcon. The wells typically have a capacity of from about 1 ml to about 4 ml. As discussed above, the number of DCs per well is typically 1.1-4.5×10$^4$.

The flask, vessel or wells within which the population is contained or cultured may be modified to facilitate handling of the iPSCs and/or DCs. For instance, the flask, vessel or wells may be modified to facilitate culture of the cells, for instance by including a growth matrix. The flask, vessel or wells may be modified to allow attachment of the iPSCs and/or DCs or to allow immobilization of the DCs onto a surface. One or more surfaces may be coated with extracellular matrix proteins such as laminin or collagen or any other capture molecules that bind to the cells and immobilize or capture them on the surface(s).

The population may be modified ex vivo using any of the techniques described herein. The population may then be used in the methods of treatment discussed in more detail below. The invention therefore provides a population of DCs of the invention loaded or transfected with an antigen. The invention further provides a population of DCs of the invention which comprise a nucleic acid encoding an antigen. The invention also provides a population of DCs of the invention which have been infected by a virus particle or another vector capable of expressing an antigen.

Method of Producing A DC of the Invention

The invention also provides a method for producing a population of the invention, i.e. a population of two or more DCs of the invention. The method involves culturing human iPSCs under conditions which induce the iPSCs to differentiate into DCs and thereby producing a population of the invention.

Induced pluripotent stem cells and methods of producing them are known in the art. A method for inducing pluripotency of differentiated cells, such as somatic cells, was first disclosed by Yamanaka (WO 2007/069666). In this method, somatic cells are reprogrammed using three main nuclear reprogramming factors, namely an Oct family gene, a K1f family gene and a Sox family gene (preferably Sox2). The factors are preferably Oct3/4, K1f4 and Sox2. A fourth reprogramming factor, namely the product of a Myc family gene (preferably c-Myc), may also be used. Numerous different methods have since been disclosed for inducing pluripotency in somatic cells. Such methods are reviewed in Hanna et al., Cell. 2010 Nov. 12; 143 (4):508-25; and Stadtfeld & Hochedlinger, Genes Dev. 2010 Oct. 15; 24 (20):2239-63. A preferred method is described in Carpenter, L. et al. *Blood* In Press (2011).

The iPSCs cells typically display the characteristic morphology of human embryonic stem cells (hESCs), express the pluripotency-associated markers SSEA-4 and TRA1-60, the transcription factors Oct-4 and Nanog and differentiate in vitro into cell types derived from each of the three embryonic germ layers. The iPSCs may be an established cell line. More preferably, the iPSCs are produced from somatic cells taken from a patient to be treated in accordance with the invention.

The iPSCs may be derived from any human somatic cell. Suitable cells include, but are not limited to, keratinocytes, dermal fibroblasts or leukocytes derived from peripheral blood. The iPSCs are preferably derived from dermal fibroblasts.

Techniques for culturing iPSCs are well known to a person skilled in the art. Suitable conditions are discussed above.

Conditions suitable for inducing stem cells to differentiate into DCs are known in the art. For instance, suitable conditions are disclosed in Tseng, S-Y. et al. *Regen. Med.* 4, 513-526 (2009). However, it is surprising that culturing human iPSCs under these condition results in DCs that are capable of cross presenting an antigen to naïve CD8$^+$ T lymphocytes.

In a preferred embodiment, the method comprises (a) culturing the iPSCs in a medium comprising granulocyte macrophage-colony stimulating factor (GM-CSF) for sufficient time to produce monocytic cells, (b) culturing the monocytic cells under conditions that induce the formation of immature dendritic cells and (c) culturing the immature dendritic cells in a medium comprising growth factors that induce maturation of the dendritic cells.

The sufficient time in step (a) is typically from 13 to 17 days. In step (a), the medium preferably further comprises one or more of stem cell factor (SCF), vascular endothelial growth factor (VEGF) and bone morphogenic protein (BMP-4). The medium more preferably initially comprises all three of SCF, VEGF and BMP-4 and each is successively removed. Step (a) most preferably comprises initially culturing the iPSCs in a medium comprising GM-CSF, SCF, VEGF and BMP-4, removing BMP-4 from day 5 onwards, removing VEGF from day 14 onwards and removing SCF from day 19 onwards until monocytic cells are produced.

The sufficient time in step (b) is typically from 9 to 15 days. Suitable conditions for forming immature DCs from monocytic cells are known in the art. Step (b) preferably involves culturing the monocytic cells in a medium comprising GM-CSF and interleukin-4 (IL-4) for sufficient time to produce immature DCs.

Step (c) takes from 36 hours to 4 days, preferably about 2 days (48 hours). The medium in step (c) preferably comprises GM-CSF, tumor necrosis factor-α (TNFα), prostaglandin-$E_2$ ($PGE_2$), interleukin-1β (IL-1β) and interferon-γ (IFNγ).

Steps (a) to (c) typically take from 21 to 32 days.

Preferred concentrations of the various growth factors are as follows:

GM-CSF—from 25 to 75 ng/ml, more preferably 50 ng/ml;
SCF—from 10 to 30 ng/ml, more preferably 20 ng/ml;
VEGF—from 25 to 75 ng/ml, more preferably 50 ng/ml;
BMP-4—from 25 to 75 ng/ml, more preferably 50 ng/ml;
IL-4—from 10 to 150 ng/ml, more preferably 25 or 100 ng/ml;
TNFα—from 10 to 30 ng/ml, more preferably 20 ng/ml;
$PGE_2$—from 0.5 to 1.5 ng/ml, more preferably 1.0 ng/ml;
IL-1β—from 5 to 15 ng/ml, more preferably 10 ng/ml; and
IFNγ—from 10 to 20 ng/ml, more preferably 15 ng/ml.

The growth factors used in the method of the invention are typically the human forms. The growth factors used in the method of the invention are typically recombinant. The use of such factors means that the DCs of the invention are produced in clinically relevant conditions, i.e. in the absence of trace amounts of endotoxins and other environmental contaminants, such as lipopolysaccharides, lipopeptides and peptidoglycans, etc. This makes the DCs of the invention particularly suitable for administration to patients.

The method preferably further comprises isolating the DCs of the invention. Any of the methods discussed above may be used.

The invention also provides a method for producing a population of the invention that is suitable for administration to a patient, wherein the method comprises producing iPSCs from somatic cells obtained from the patient and producing a population of the invention from those iPSCs using the method of the invention described above. The population will be autologous with the patient and therefore will not be rejected upon implantation. The invention also provides a population of the invention that is suitable for administration to a patient and is produced in this manner. Alternatively, the invention provides a method for producing a population of the invention that is suitable for administration to a patient, wherein the method comprises the differentiation of partially-matched iPSCs obtained from a public bank of clinically-approved lines.

Medicaments, Methods and Therapeutic Use

The DCs of the invention may be used in a method of therapy of the human or animal body. Thus the invention provides a DC of the invention or a population of the invention for use in a method of treatment of the human or animal body by therapy. In particular, the invention concerns using the DCs of the invention to induce a CTL response to an antigen in a patient. The antigen may be derived from a tumor or a pathogen. In one embodiment, the induced CTL response will help to remove the tumor or the pathogen from the patient (i.e. the CTL response is therapeutic).

In all instances, the DCs of the invention are preferably derived from the patient or an individual that is matched with the patient at one or more of the MHC restriction elements required for presentation of the antigen. Deriving the DCs of the invention from the patient (via iPSCs) should ensure that the DCs are themselves not rejected by the patient's immune system. Any difference between the donor and recipient will ultimately cause clearance of the DCs, but not before they have stimulated a potent antigen-specific response The invention provides a method of inducing a CTL response to an antigen in a patient in need thereof, comprising administering to the patient an immunologically effective number of DCs of the invention which are loaded or transfected with the antigen and thereby inducing a CTL response to the antigen in the patient. An immunologically effective number is a number which induces a CTL response to the antigen in the patient. The invention also provides a DC of the invention or a population of the invention for use in a method of inducing a CTL response to an antigen in a patient in need thereof, wherein the DC(s) are loaded or transfected with the antigen. The invention also provides use of a DC of the invention or a population of the invention in the manufacture of a medicament for inducing a CTL response to an antigen in a patient in need thereof, wherein the DC(s) are loaded or transfected with the antigen. The antigen may be any protein, polypeptide or peptide. Suitable antigens are discussed below with reference to tumors and pathogens. In all embodiments, the CTL response is preferably a $CD8^+$ CTL response. In all embodiments, the CTL response may be therapeutic (i.e. treating a disease or condition in the patient).

In one embodiment, the antigen is a tumor antigen and the method is for treating or preventing a tumor in the patient. Hence, the invention provides a method of treating a tumor in a patient in need thereof, comprising administering to the patient a therapeutically effective number of DCs of the invention which are loaded or transfected with an antigen from the tumor and thereby inducing a CTL response to the antigen in the patient and treating the tumor. A therapeutically effective number is a number effective to ameliorate one or more symptoms of the tumor. Typically, such a number removes the tumor from the patient.

The invention also provides a DC of the invention or a population of the invention for use in a method of treating a tumor in a patient in need thereof by inducing a CTL response to an antigen from the tumor in the patient, wherein the DC(s) are loaded or transfected with the antigen. The invention also provides use of a DC of the invention or a population of the invention in the manufacture of a medicament for treating a tumor in a patient in need thereof by inducing a CTL response to an antigen from the tumor in the patient, wherein the DC(s) are loaded or transfected with the antigen.

Tumors from which the antigen may be derived include, but are not limited to, melanoma, lymphoma and leukaemia or tumors of the lung, prostate, breast, colon and ovary. Suitable tumor antigens include, but are not limited to, Melan-A, tyrosinase, p97, beta-HCG, GalNAc, MAGE-1, MAGE-2, MAGE-4, MAGE-12, MUC1, MUC2, MUC3, MUC4, MUC18, CEA, DDC, P1A, EpCam, melanoma antigen gp75, Hker 8, high molecular weight melanoma antigen, K19, Tyr1, Tyr2, members of the pMel 17 gene family, c-Met, PSA (prostate antigen), PSM (prostate mucin antigen), PSMA (prostate specific membrane antigen), prostate secretary protein, alpha-fetoprotein, CA125, CA19.9, TAG-72, BRCA-1 and BRCA-2 antigens. If the invention concerns treating a tumor in a patient, the antigen I is preferably obtained from the tumor itself, for instance extracted by biopsy and identified in vitro.

In another embodiment, the antigen is from a pathogen and the method is for treating an infection by the pathogen in the patient. Hence, the invention provides a method of treating a pathogenic infection in a patient in need thereof, comprising administering to the patient a therapeutically effective number of DCs of the invention which are loaded or transfected with an antigen from the pathogen and thereby inducing a CTL response to the antigen in the patient and treating the infection. A therapeutically effective number is a number effective to ameliorate one or more symptoms of the infection. Typically, such a number removes the pathogen from the patient.

The invention also provides a DC of the invention or a population of the invention for use in a method of treating a pathogenic infection in a patient in need thereof by inducing a CTL response to an antigen from the pathogen in the patient, wherein the DC(s) are loaded or transfected with the antigen. The invention also provides use of a DC of the invention or a population of the invention in the manufacture of a medicament for treating a pathogenic infection in a patient in need thereof by inducing a CTL response to an antigen from the pathogen in the patient, wherein the DC(s) are loaded or transfected with the antigen. Suitable pathogens that may be treated or prevented in accordance with the invention include, but are not limited to, bacteria, such as *Mycobacterium tuberculosis*, viruses, such as HIV, parasites, protozoans, such as *Plasmodium falciparum* and fungi. Typically, such microorganisms will establish chronic infections that are resistant to conventional treatment.

In another embodiment, the method is for removing immunological tolerance to the antigen. The antigen is typically a self antigen or a tumor antigen. The antigen may be any of the tumor antigens discussed above. One of the main barriers to inducing an effective immune response to tumor antigens is self tolerance since tumor antigens are self molecules rather than pathogen derived. This self tolerance is often maintained by regulatory T cells (Treg) specific for the antigens which inhibit the priming of effector T cells specific for the same antigens. Nevertheless, Treg are relatively unstable and may, in response to IL-6, convert to Th17 cells, which are strongly pro-inflammatory. Th17 cells secrete IL-17. Since the DCs of the invention secrete high levels of IL-6 upon maturation, they are capable of bypassing the Treg barrier, converting Treg to Th17 cells and thereby removing immunological tolerance to the antigen.

In another embodiment, the invention provides a method of inducing tolerance to an antigen in a patient in need thereof, comprising administering to the patient an immunologically effective number of immature DCs produced using the method of the invention or DCs of the invention which have been treated to render them tolerogenic and thereby inducing tolerance to the antigen in the patient, wherein the DCs are loaded or transfected with the antigen. Immature DCs produced using the invention can be used for the induction of tolerance, for example to autoantigens or therapeutic proteins. The immature DCs are produced by (a) culturing iPSCs in a medium comprising granulocyte macrophage-colony stimulating factor (GM-CSF) for sufficient time to produce monocytic cells and (b) culturing the monocytic cells under conditions that induce formation of immature dendritic cells. Any of the embodiments discussed above may be used. Similarly, DCs of the invention can be used to induce tolerance to the antigen following treatment to render them tolerogenic, such as with vitamin D3, dexamethasone, IL-10 or rapamycin. The immature DCs or pharmacologically-treated DCs of the invention induce the polarisation of naïve T cells towards a Treg phenotype which will maintain the tolerant state. An immunologically effective number is a number which induces tolerance to the antigen in the patient.

The invention also provides (a) an immature DC or immature DCs produced using the method of the invention or (b) a DC of the invention or DCs of the invention which have been treated to render them tolerogenic for use in a method of inducing tolerance to an antigen in a patient in need thereof, wherein the DC(s) are loaded or transfected with the antigen. The invention also provides use of (a) an immature DC or immature DCs produced using the method of the invention or (b) a DC of the invention or DCs of the invention which have been treated to render them tolerogenic in the manufacture of a medicament for inducing tolerance to an antigen in a patient in need thereof, wherein the DC(s) are loaded or transfected with the antigen. The antigen is preferably involved in an autoimmune disease in the patient or will facilitate cell replacement therapy for the correction of a congenital condition in the patient.

Immunisation results in promoting an immune response against the chosen antigen. Any of the effects resulting from the loaded or transfected DCs mentioned herein may be promoted or achieved. In particular, the level of presentation of the chosen antigen will be increased in the patient. An increase in presentation via MHC I and/or MHC II molecules and in particular via MHC I molecules in the patient will typically be seen. In a preferred case, the level of antigen presentation achieved may be such that when the same antigen is encountered again an increased immune response is seen in comparison to the situation in which the initial immunisation had not taken place. In particular, a therapeutic and/or protective immune response is raised. The invention may, therefore, ensure that a higher level of immune response is seen when the antigen is next encountered, for instance, upon serial administration of the population of DCs, in order to further boost responses to the antigen.

The invention may be used to enhance the level of antigen presentation or of any of the downstream effects thereof, such as any of those mentioned herein, in comparison to administration of an equivalent amount of antigen in the absence of loaded or transfected DCs. The increase may be double, treble, or more fold, in some cases it may be at least ten-fold, preferably at least twenty-fold and even more preferably at least 100 fold, or 1000 fold or more. It may be that a therapeutic response is seen whereas, in the absence of the use of loaded or transfected DCs, it is not.

The loaded or transfected DCs may be administered to any suitable patient. The patient is generally a human patient. The patient may be an infant, a juvenile or an adult. In one embodiment, the patient is susceptible to, or at risk from, the relevant disease. For instance, the patient may be genetically predisposed to developing the tumor. Alternatively, the patient may have been exposed, or will be in a region where there is a risk of exposure, to a particular antigen and in particular a pathogen, for example, the vertical transmission of HIV-1 from mother to child.

The invention may be used in combination with other means of, and substances for, immunisation. In some cases the loaded or transfected DCs may be administered simultaneously, sequentially or separately with antigen which is not present in loaded or transfected DCs (i.e. free antigen). The loaded or transfected DCs may be used in combination with existing vaccines for a particular antigen and may, for example, be simply mixed with such vaccines. Thus the invention may be used to increase the efficacy of existing vaccines including, for example, peptide, polypeptide, protein, nucleic acid, viral and/or bacterial based antigens.

In a preferred embodiment, the loaded or transfected DCs are administered simultaneously, sequentially or separately with one or more ligands of the Toll-like receptors (TLRs). This will improve the ability of the DCs to cross present antigen in vivo. Suitable ligands include, but are not limited to, 2'-deoxyribo(cytidine-phosphoguanosine) (CpG) DNA motifs, polyinosinic-polycytidylic acids (poly(I:Cs)), lipopeptides, peptidoglycans, lipoteichoic acid, lipoarabinomannan, zymosan, tGPI-mucin, hemagglutinin protein and lipopolysaccharides.

The invention concerns the use of loaded or transfected DCs. The DCs may be loaded or transfected using any method known in the art. The loading of DCs may be performed in vitro or ex vivo. In each case, the DCs may simply be in contact with the antigen in culture. The DCs of the invention are capable of endocytosing, phagocytosing or otherwise taking up exogenous peptide polypeptide or protein antigens and, after internalisation and processing, presenting antigenic peptide fragments on their surface, bound to products of the MHC. Alternatively, the DCs may be loaded with antigen using monoclonal antibodies specific for surface molecules, such as CD205 and DNGR-1. Such molecules are known in the art.

The transfection of DCs may be performed in vitro or ex vivo. Alternatively, stable transfection may be performed at the iPSC stage allowing DCs expressing the transgene to be differentiated from them. The DCs are transfected with a nucleic acid encoding the antigen. For instance, viral particles or other vectors encoding the antigen may be employed. Methods for doing this are known in the art.

The nucleic acid gives rise to expression of the antigen in the DCs and to the subsequent presentation of the antigen by the cells. The nucleic acid molecule will preferably comprise a promoter which is operably linked to the sequences encoding the antigen and which is active in the DCs or which can be induced in the DCs.

In a particularly preferred embodiment, the nucleic acid encoding the antigen may be delivered via a viral particle. The viral particle may comprise a targeting molecule to ensure efficient transfection. The targeting molecule will typically be provided wholly or partly on the surface of the virus in order for the molecule to be able to target the virus to the DCs.

Any suitable virus may be used in such embodiments. The virus may, for example, be a retrovirus, a lentivirus, an adenovirus, an adeno-associated virus, a vaccinia virus or a herpes simplex virus. In a particularly preferred embodiment the virus may be a lentivirus. The lentivirus may be a modified HIV virus suitable for use in delivering genes. The lentivirus may be a SIV, FIV, or equine infectious anemia virus (EQIA) based vector. The virus may be a moloney murine leukaemia virus (MMLV). The viruses used in the invention are preferably replication deficient.

Viral particles do not have to be used. Any vector capable of transfecting the DCs of the invention may be used, such as conventional plasmid DNA or RNA transfection.

The nucleic acid molecule may also encode other sequences, for example the nucleic acid may comprise sequences which express proteins which boost the immune response to the antigen. The nucleic acid may encode a cytokine, including any of those mentioned herein and in particular IL-1, IL-2 and/or IL-12. The nucleic acid may also encode a costimulatory molecule such as a cell-surface molecule which enhances the immune response. The nucleic acid may encode, for example, CD80 and/or CD86. The nucleic acid molecule preferably encodes one or more of the Toll-like receptor ligands disclosed herein.

Uptake of nucleic acid constructs may be enhanced by several known transfection techniques, for example those including the use of transfection agents. Examples of these agents includes cationic agents, for example, calcium phosphate and DEAE-Dextran and lipofectants, for example, lipofectAmine, fugene and transfectam.

The cell may be loaded or transfected under suitable conditions. The cell and antigen or vector may, for example, be contacted for between five minutes and ten days, preferably from an hour to five days, more preferably from five hours to two days and even more preferably from twelve hours to one day.

The invention also provides DCs which have been loaded or transfected with an antigen. Such DCs may be used in the therapeutic embodiments of the invention. The loaded or transfected cells may comprise epitopes of the antigen. The cells may also comprise a targeting molecule and/or breakdown products thereof. The invention provides such cells in an isolated form as discussed above. The transfected cells may comprise a nucleic acid encoding the antigen and, in particular, may comprise a viral vector encoding the antigen. Preferably, the viral vector will be replication deficient.

Generally the loaded or transfected DCs carry peptides, and in particular an antigenic epitope derived from the chosen antigen on their surface in conjunction with an MHC class I or class II molecule and in particular in conjunction with an MHC I molecule. In one embodiment each DC has at least 100, preferably at least 200, for example at least or about 500 or 1000, class I and/or class II molecules on its surface loaded with the product and in particular class I molecules. In some cases, the DCs may carry a label or be labelled, such as, for example, with a fluorescent molecule such as green fluorescent protein (GFP).

In some embodiments, somatic cells may be recovered from the patient, converted into DCs using the invention, loaded or transfected in vitro and then returned to the same subject. In such instances, the DCs employed in the invention, will be autologous cells and fully matched with the patient for MHC class I HLA-A or HLA-B; and/or for MHC class II type. In a preferred case, the cells employed in the invention are recovered from a patient and utilised ex vivo and subsequently returned to the same patient.

In another embodiment, iPSCs may be selected from a public bank of clinically-approved lines in order to ensure that they share with the patient one or more MHC molecules required for presentation of the designated antigen to the immune system of the recipient.

Pharmaceutical Compositions, Vaccines and Administration

The invention additionally provides a pharmaceutical composition comprising (a) a DC of the invention or a population of DCs of the invention and (b) a pharmaceutically acceptable carrier or diluent. The present invention also provides a vaccine composition comprising a DC or population of DCs of the invention. The vaccines and compositions may comprise any of the DCs or populations mentioned herein and, in come embodiments, the nucleic acid molecules, vectors, viruses or antigens described herein. The invention provides a method of vaccination comprising administering to a patient an effective amount of a vaccine composition of the invention.

The various compositions and vaccines of the invention may be formulated using any suitable method. Formulation of cells with standard pharmaceutically acceptable carriers and/or excipients may be carried out using routine methods in the pharmaceutical art. The exact nature of a formulation will depend upon several factors including the cells to be administered and the desired route of administration. Suitable types of formulation are fully described in Remington's Pharmaceutical Sciences, 19$^{th}$ Edition, Mack Publishing Company, Eastern Pennsylvania, USA.

The cells may be administered by any route. Suitable routes include, but are not limited to, intravenous, intramuscular, intraperitoneal or other appropriate administration routes. The cells are preferably administered to sites of antigen presentation, such as draining lymph nodes.

Compositions and vaccines may be prepared together with a physiologically acceptable carrier or diluent. Typically, such compositions and vaccines are prepared as liquid suspensions of cells. The cells may be mixed with an excipient which is pharmaceutically acceptable and compatible with the active ingredient. Suitable excipients are, for example, water, saline, dextrose, glycerol, of the like and combinations thereof.

In addition, if desired, the vaccine and/or pharmaceutical compositions of the invention may contain minor amounts of auxiliary substances such as wetting or emulsifying agents, pH buffering agents, and/or adjuvants which enhance effectiveness.

In some embodiments, the pharmaceutical composition or vaccine may comprise an adjuvant. In other words, an adjuvant may be present in the various formulations of the invention or be administered simultaneously, separately or sequentially with them. Suitable adjuvants include, for example, any substance that enhances the immune response of the subject to the antigen (including when delivered by the polynucleotide of the invention). They may enhance the immune response by affecting any number of pathways, for example, by stabilizing the antigen/MHC complex, by causing more antigen/MHC complex to be present on the cell surface, by enhancing maturation of DCs, or by prolonging the life of APCs (e. g., inhibiting apoptosis).

Examples of adjuvants that may be employed include cytokines. Certain cytokines, for example TRANCE, flt-3L, or agents such as CD40L, enhance the immunostimulatory capacity of antigen presenting cells and may be employed. Non-limiting examples of cytokines which may be used alone or in combination include, interleukin-2 (IL-2), interleukin-3 (IL-3), interleukin 6 (IL-6), interleukin-12 (IL-12), G-CSF, granulocyte macrophage-colony stimulating factor (GM-CSF), interleukin-1α (IL-1α), interleukin-11 (IL-11), c-kit ligand, thrombopoietin (TPO), CD40 ligand (CD40L), tumor necrosis factor-related activation-induced cytokine (TRANCE) and flt3 ligand (flt-3L). Further examples of adjuvants which may be effective include but are not limited to: aluminium hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. Especially preferred adjuvants include the ligands of the Toll-like receptors discussed above.

In cases where the invention uses DCs transfected with a nucleic acid which encodes an antigen, the nucleic acid may also encode molecules capable of acting as an adjuvant. Thus the nucleic acid may lead to the production of any of the adjuvants mentioned herein and in particular a cytokine or costimulatory molecule. The cytokine may, for example be, IL-1, IL-2, and/or IL-12 which will preferably be secreted from the antigen presenting cell. The costimulatory molecule may, for example, be CD80 or CD86 which will be preferably expressed on the cell surface of the DCs.

The DCs are administered in a manner compatible with the dosage formulation and in such amount will be immunologically, prophylactically and/or therapeutically effective. The quantity to be administered depends on the subject to be treated, capacity of the subject's immune system to respond to the antigen, and the degree of CTL response desired. Precise amounts of DCs required to be administered may depend on the judgement of the practitioner and may be peculiar to each subject.

The methods described herein are preferably carried out in conjunction with standard chemotherapy or radiotherapy. Such therapies have been shown to act synergistically with cell vaccination strategies, such as the methods of the invention. Dying tumor cells release a source of the tumor antigens helping to sustain the immune response generated by cell vaccination.

Any suitable number of cells may be administered to a subject. For example, at least, or about, $10^5$, $10^6$, $10^7$, $10^8$, $10^9$ cells may be administered. As a guide, the number of cells of the invention to be administered may be from $10^5$ to $10^9$, preferably from $10^6$ to $10^8$. Any of the specific numbers discussed above with reference to the populations of the invention may be administered. In such cases where cells are administered or present, culture medium may be present to facilitate the survival of the cells. In some cases the cells of the invention may be provided in frozen aliquots and substances such as DMSO may be present to facilitate survival during freezing. Such frozen cells will typically be thawed and then placed in a buffer or medium either for maintenance or for administration.

The following Example illustrates the invention.

EXAMPLE

Materials and Methods

Derivation and Culture of Human Induced Pluripotent Stem Cells

Human iPSC were derived, maintained and their pluripotency assessed. Cells were cultured in 6 well plates in a volume of 4 ml per well and the medium replaced daily, except on the day following their passage. Plates were coated with matrigel (BD Biosciences) diluted 1:30 and stored at 4° C. until use. hiPSC cultured in mTeSR1 (Stem-Cell Technologies) were routinely passaged every 6-7 days at a 1:12 dilution, while hiPSC maintained in TeSR2 (Stem-Cell Technologies) were passaged every 5-6 days at a dilution of 1:12-1:15.

Directed Differentiation of DC

Briefly, the differentiation medium consisted of XVIVO-15 (Lonza) supplemented with non-essential amino acids, 2 mM L-glutamine, 1 mM sodium pyruvate (PAA Laboratories GmbH), $5 \times 10^{-5}$ M 2-mercaptoethanol (Sigma), granulocyte macrophage-colony stimulating factor (GM-CSF; 50 ng/ml) (Peprotech), stem cell factor (SCF; 20 ng/ml) (R&D Systems), vascular endothelial growth factor (VEGF; 50 ng/ml) (Peprotech) and bone morphogenetic protein-4 (BMP-4; 50 ng/ml) (R&D Systems) that were successively removed from cultures until only GM-CSF remained. BMP-4 was removed from day 5 onwards, followed by VEGF (day 14) and SCF (day 19). On days 13-17 of culture, the medium was supplemented with 25 ng/ml of recombinant human interleukin-4 (rhIL-4) (Peprotech). The concentration of IL-4 in the medium was increased to 100 ng/ml as numbers of DC accumulated in the cultures (days 20-24). DC were harvested on days 24-28 using gentle pipetting, passed through a 70 µm cell strainer (BD Falcon) and plated at $5 \times 10^5 - 1 \times 10^6$ per well of a 6-well CellBind plate (Corning) in complete XVIVO-15 medium containing 50 ng/ml GM-CSF and 100 ng/ml IL-4. After 2-4 days, DC were matured for the final 48 h of culture, as described[10] with a cocktail of cytokines consisting of TNFα (50 ng/ml), PGE$_2$ (1 µg/ml), IL-1β (10 ng/ml) and IFN-γ (20 ng/ml).

Isolation and Culture of Primary Cells

Monocytes and naïve T cells were isolated from the peripheral blood mononuclear cells (PBMC) of buffy coats (NHS blood transfusion service) or the fresh blood of volunteers using CD14-coated beads or a pan T cell selection kit followed by depletion of CD45RO$^+$ memory cells using the relevant selection kits/beads (Miltenyi Biotech). AutoMACs separation was used to either positively select or deplete labelled populations of PBMC according to the manufacturer's instructions. Following removal of CD14$^+$ monocytes, peripheral blood lymphocytes (PBL) were cultured in RPMI supplemented with 10% fetal calf serum (FCS), 50 U/ml penicillin, 50 µg/ml streptomycin and 2 mM L-glutamine (PAA Laboratories GmbH) (R10). Monocyte derived DC (moDC) were differentiated by culturing CD14$^+$ monocytes in R10 containing 50 ng/ml GM-CSF and 100 ng/ml IL-4 for 6-8 days.

Flow Cytometry

DC or hiPSC were incubated for 15 min on ice in blocking buffer (PBS, 5% normal rabbit serum, 0.5% bovine serum albumin (BSA), 0.1% NaN$_3$) and washed twice. Cells were stained on ice in PBS/2% FCS for 30 min with one of the following antibodies: TRA1-60 (Millipore), SSEA-4 (clone: MC-813-70, R&D Systems), HLA-A2 (BB7.2), CD11c (BU15), CD11b (ICRF44), HLA-DR/DQ/DP (WR18), CD40 (LOB7/6) (AbD Serotec), CD123 (9F5, BD Pharmingen), BDCA-4 (446921), BDCA-2 (polyclonal goat IgG), BDCA-3 (501733) (R&D Systems), CD83 (HB15e), CD80 (MEM-233), CD86 (BU63), CD14 (MEM18), CD54 (15.2, AbD Serotec), CCR7 (3D12, eBioscience), XCR1 (polyclonal goat IgG; R&D Systems). For the final 10 min, 7-AAD was added at a concentration of 250 ng/ml. Cells were washed twice and fixed in 2% formaldehyde.

Intranuclear staining was performed using commercial permeabilisation and fixation buffers (eBiosciences), according to the manufacturer's instructions together with antibodies specific for the transcription factors Oct-4 (240408) or Nanog (polyclonal goat IgG; R&D Systems). T cells were labelled with tetramer as described[14] and stained for intracellular cytokines. Briefly, T cells were first labelled with HLA-A*0201-MelanA$_{26-35}$ tetramer and were untreated or stimulated with either 20 µM Melan A$_{26-35}$ peptide or 50 ng/ml PMA and 500 µg/ml ionomycin (Sigma) for 6 h, as a positive control. For the final 4 h of culture, 10 µg/ml Brefeldin A (Sigma) was added. Cells were washed, surface stained for CD8 and fixed in 2% paraformaldehyde. Buffer containing saponin (PBS, 0.5% saponin, 0.5% BSA, NaN$_3$; Sigma) was used to wash cells twice before staining for IFN-γ (25723, R&D Systems) or perforin (dG9, eBioscience). Cells were washed twice before analysis on a Beckton Dickinson FACSCalibur.

Antigen Processing and Presentation Assay

DC were harvested and either untreated or fixed with 0.5% paraformaldehyde for 10 min at room temperature. DC were plated at $1-1.5 \times 10^4$ cells per well in a 96-well flat bottomed plate. Fixed or unfixed cells were left untreated or incubated with either 1 µM Melan A (AMS Biotechnology) or, as a positive control for antigen presentation, pulsed with either 10 nM or 1 µM Melan A$_{26-35}$ peptide (ELAGIGILTV)[14]. The CD8$^+$ T cell clone, 2D10, which is specific for the HLA-A*0201-Melan A$_{26-35}$ complex, was plated at a 1:5 ratio of DC:T cells. Co-cultures were incubated at 37° C., 5% CO$_2$ for 40 h, before supernatants were harvested.

ELISAs

IFN-γ and IL-6 ready-SET-go ELISA kits and immunosorb plates were purchased from eBiosciences and ELISAs were performed according to the manufacturer's instructions. ELISAs were read at 450 nm using a BioTek EL$_x$808 plate reader.

In Vitro Priming of Naive Antigen Specific T Cells

Harvested HLA-A*0201$^+$ moDC and ipDC were either untreated or pulsed with 1 µM Melan A$_{26-35}$ peptide for 2½-3 h and washed. DC were plated at $4 \times 10^4$ per well of a 48-well plate or $1 \times 10^5$ per well of a 24-well plate and unpulsed cells were either treated with 1 µM whole Melan A protein or left untreated. DC were cultured together with HLA-A*0201-restricted naïve T cells from a different donor to the moDC to yield a ratio of 1:10 DC:T cells. Cells were cultured at 37° C., 5% CO$_2$ for 13-14 days in RPMI containing 5% human male AB serum (Sigma), 50 U/ml penicillin, 50 U/ml streptomycin and 2 mM L-glutamine. Recombinant human interleukin-2 (rhIL-2) was added at 10 U/ml from days 4-7 and T cells were expanded using 500 U/ml rhIL-2 for the remainder of the culture period.

Results

The C19 iPSC line was derived from the dermal fibroblasts of an HLA-A2$^+$ donor as described (Carpenter, L. et al. Blood In Press (2011)) and was maintained long-term under feeder- and serum-free conditions.

Figure 1:
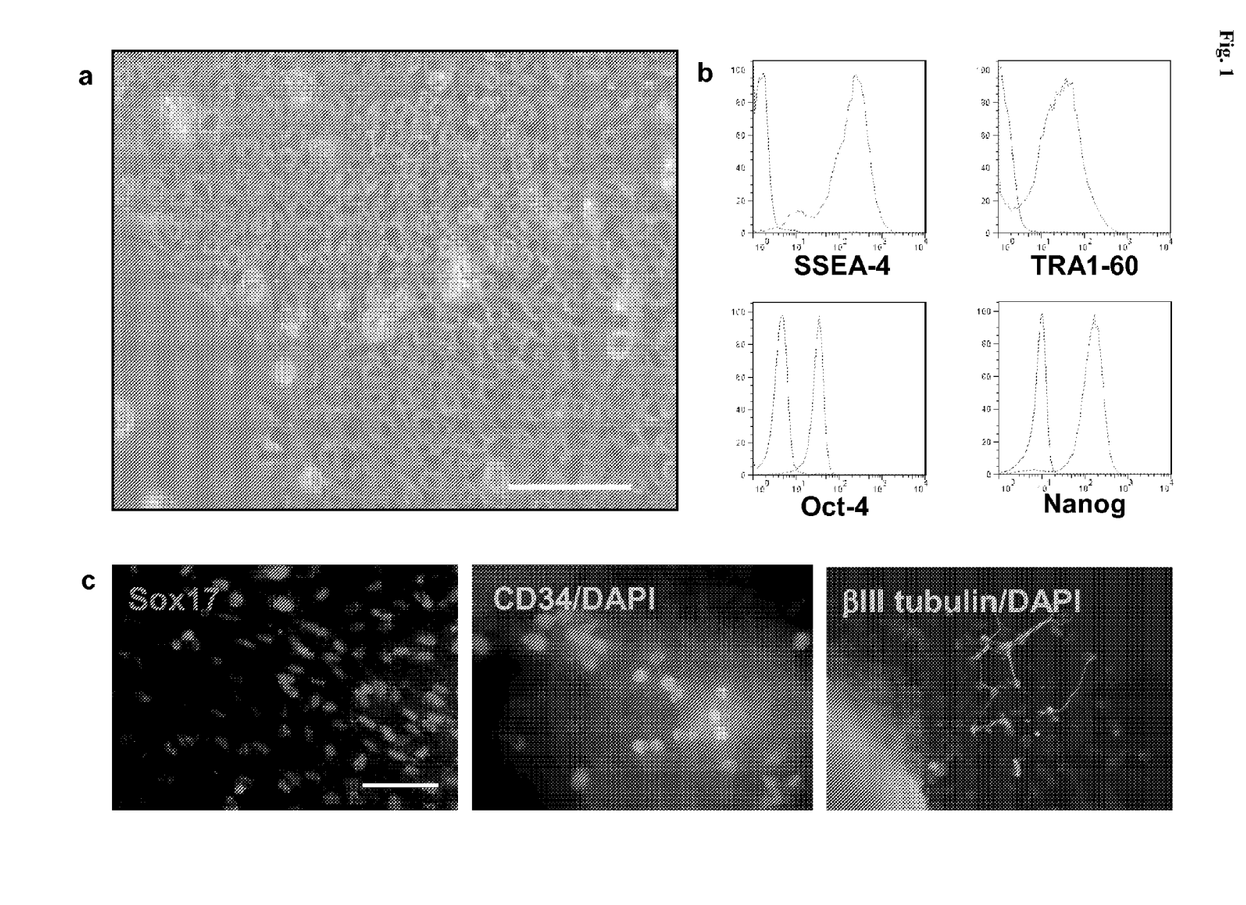

Undifferentiated C19 cells displayed the characteristic morphology of human embryonic stem cells (hESC), expressed the pluripotency-associated markers SSEA-4 and TRA1-60, the transcription factors Oct-4 and Nanog, and differentiated in vitro into cell types derived from each of the three embryonic germ layers (FIG. 1). We directed the differentiation of C19 towards the DC lineage by adapting protocols we had established previously for the differentiation of clinical grade DC from hESC.

Figure 2:
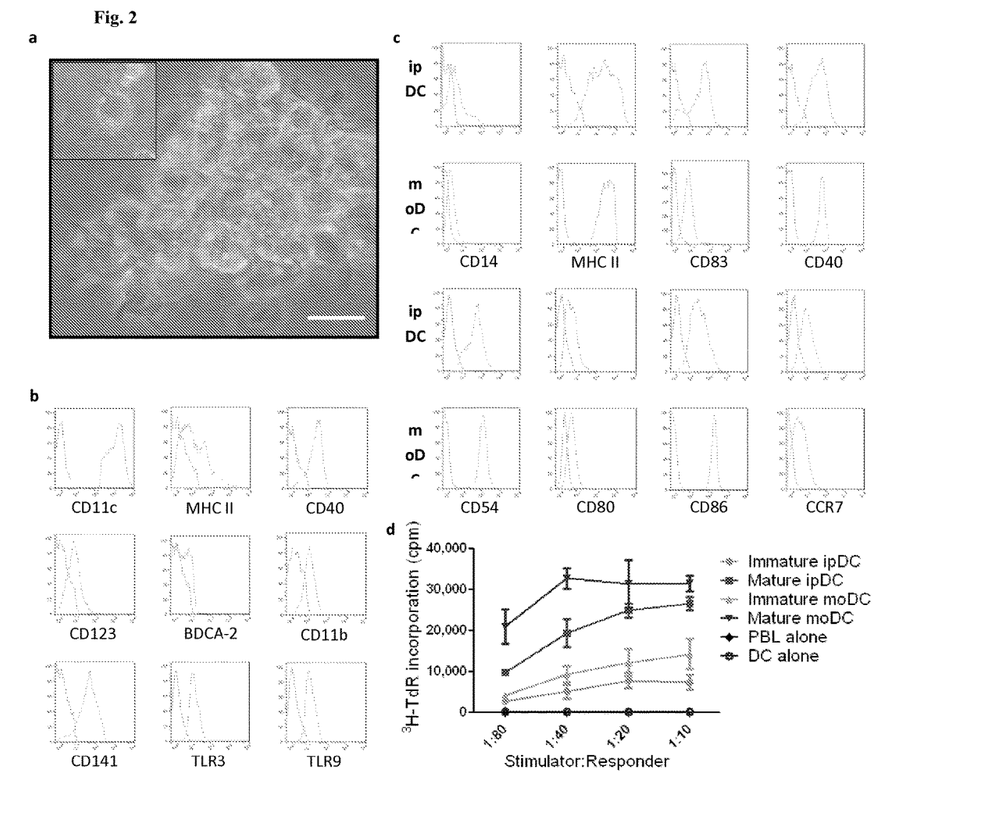
Figure 4:
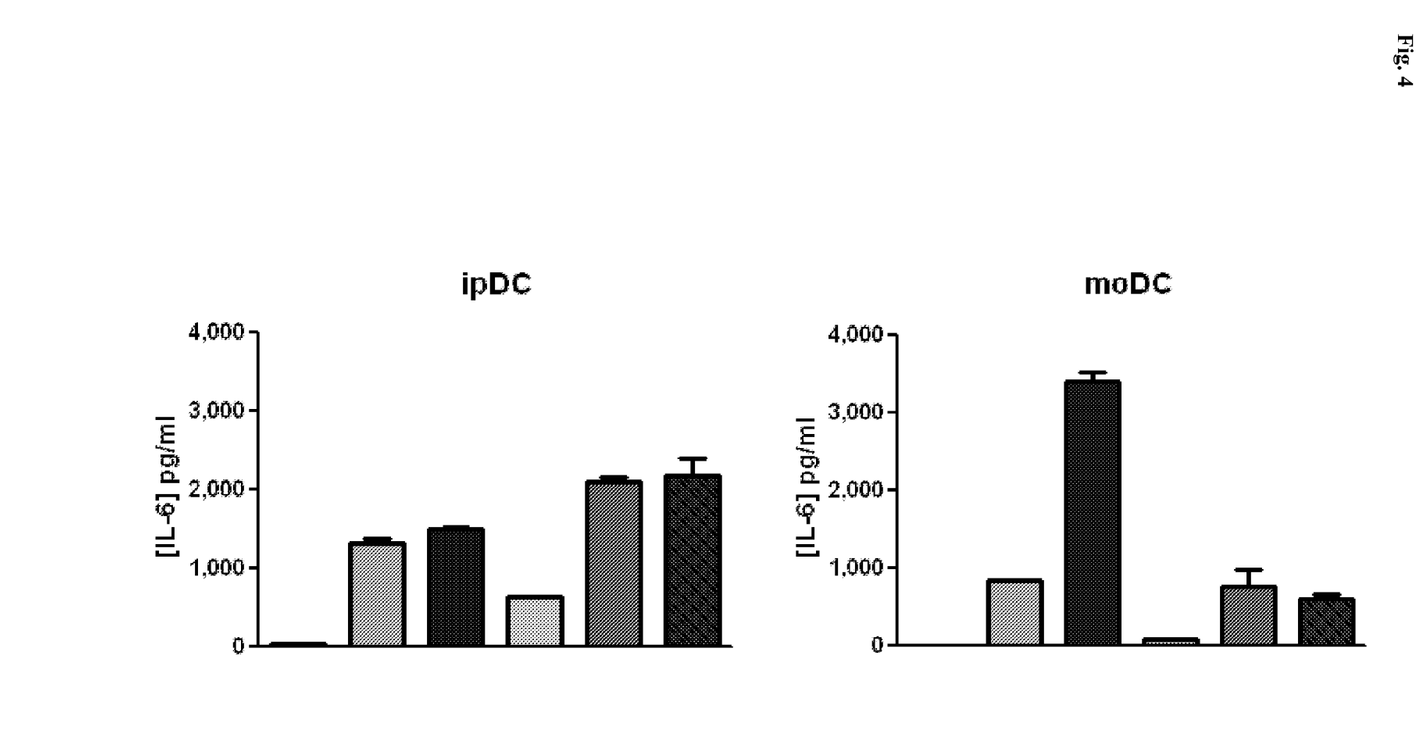
FIG. 4 shows that ipDC secrete IL-6 upon maturation in response to a cocktail of inflammatory cytokines or TLR ligands. From left to right, the columns represent unstimulated, TLR2/1Ls, TLR4L, TLR3Ls, TLR7/8L and cytokines. Both ipDC and moDC were treated with the maturation cocktail or stimulated with the TLR2/1 ligand Pam3CysSerLys4 (Pam3CSK4) at 1 μg/ml; TLR2 ligand heat killed *L. monocytogenes* (HKLM, 5×10$^4$ cells/ml); TLR4 ligand *E. coli* K12 lipopolysaccharide (1 μg/ml); TLR3 ligands Poly(I:C) and Poly(I:C) low molecular weight (LMW), both at 10 μg/ml, and the TLR7/8 ligand R848 at 2.5 μg/ml. Supernatants were collected after 40 h and IL-6 content was measured by ELISA.

After 19-24 d, cultures contained cells with distinctive dendritic morphology (FIG. 2a), expressing CD11c and low levels of both MHC class II and CD40, suggestive of an immature phenotype (FIG. 2b). In response to a maturation cocktail consisting of tumor necrosis factor-α (TNFα), prostaglandin-$E_2$ ($PGE_2$), interleukin-1β (IL-1β) and interferon-γ (IFNγ), ipDC secreted high concentrations of the pro-inflammatory cytokine IL-6 (FIG. 4). Furthermore, upon maturation, ipDC lost expression of CD14 while up-regulating MHC class II, CD83, conventional co-stimulatory molecules and the chemokine receptor, CCR7, yielding a phenotype similar to that of mature moDC (FIG. 2c). Indeed, like their counterparts, ipDC stimulated potent proliferative responses among naïve allogeneic T cells (FIG. 2d). Despite these similarities, ipDC differed phenotypically from moDC in other respects: while they lacked significant expression of the plasmacytoid DC markers CD123 and BDCA-2, ipDC displayed a $CD11b^{lo}CD141^{hi}$ phenotype, reminiscent of the recently-described population of cross-presenting DC in human blood and secondary lymphoid organs. Furthermore, these cells expressed intracellular Toll like receptors (TLR) 3 and 9 (FIG. 2b), the ligation of which promotes cross-presentation of antigen by mouse DC.

Figure 3:
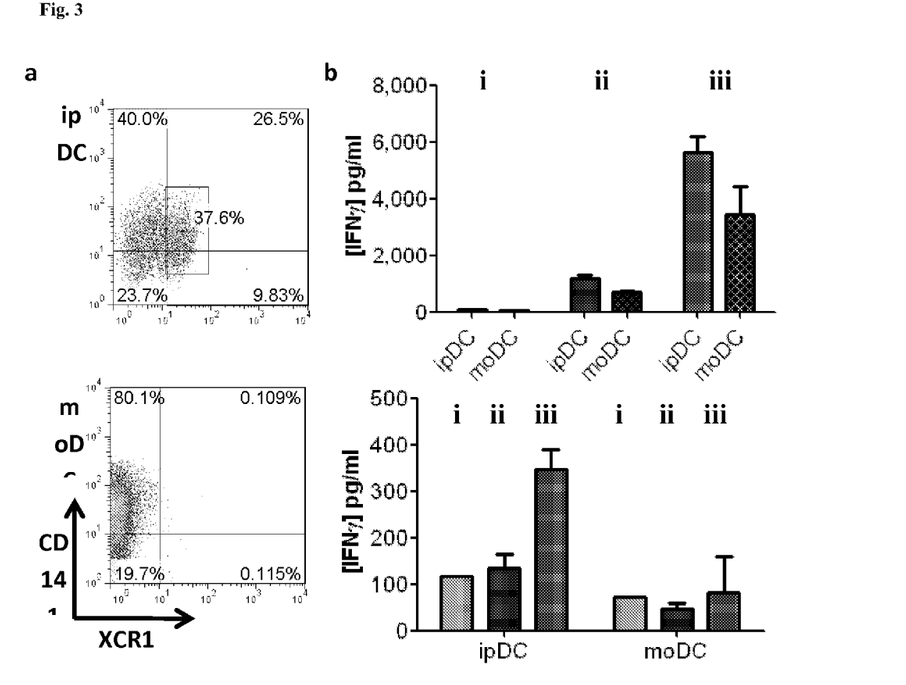

Given these findings, we investigated expression of the chemokine receptor XCR1. Although various DC populations are known to up-regulate CD141 in culture, XCR1 expression has been shown to be highly specific for cross-presenting DC in both mouse and human and to augment the antigen-driven expansion of $CD8^+$ CTL. Although moDC failed to express this chemokine receptor, ipDC consistently contained a population of cells co-expressing CD141 and XCR1 (FIG. 3a).

Figure 5:
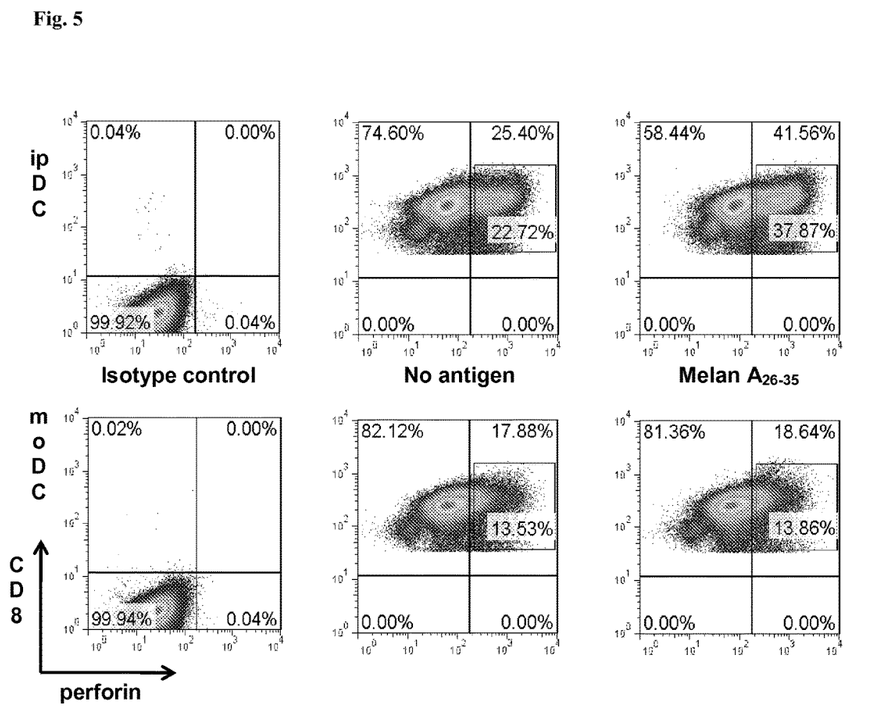

When pulsed with the HLA-A*0201-restricted peptide from the TAA Melan A (Melan $A_{26-35}$), both moDC and ipDC stimulated IFN-γ production by the $CD8^+$ T cell clone, 2D10, in a dose-dependent manner. However, when pulsed with recombinant Melan A protein as a source of unprocessed antigen, only ipDC were able to cross-present the Melan $A_{26-35}$ epitope (FIG. 3b), consistent with their $XCR1^+$ phenotype. To determine whether ipDC could prime TAA-specific responses among naïve T cells, we pulsed moDC and ipDC with Melan $A_{26-35}$ peptide and cultured them with T cells depleted of $CD45RO^+$ memory cells, purified from an HLA-$A2^+$ donor. After 14 d, T cells were stained for CD8 and with HLA-A*0201-Melan $A_{26-35}$ tetramers to detect antigen-specific T cells[14]. Whereas both moDC and ipDC primed Melan A-specific $CD8^+$ T cells when pulsed with the immunodominant epitope, only ipDC elicited a small but reproducible response when pulsed with whole Melan A protein, consistent with their capacity to cross-prime (FIG. 3c). Importantly, T cells stimulated with ipDC expressed IFN-γ (FIG. 3d) and up-regulated perforin, as evidence of their cytolytic potential (FIG. 5).

While identification of the human equivalent of murine $CD8α^+$ DC offers promise for their use in cancer immunotherapy, their presence in peripheral blood at a frequency of 1:10,000 mononuclear cells has so far posed an insurmountable barrier to their clinical application. We have employed human iPSC, capable of indefinite self-renewal, to generate potentially-unlimited numbers of such cells in vitro, using protocols compatible with their future clinical use. The ongoing construction of extensive banks of clinically-approved iPSC lines, covering the common HLA haplotypes, may permit the matching of individual patients with lines expressing appropriate MHC restriction elements for the relevant TAA. Semi-allogeneic DC differentiated from mouse ESC have been shown to stimulate potent anti-tumor responses in mice: indeed the stimulation of alloreactive T cells may provide a cytokine milieu conducive to the priming of naïve T cells specific for TAA. In this respect, the secretion of high levels of IL-6 by ipDC in response to the maturation cocktail, augurs well for breaking the regulatory T cell barrier that constitutes one of the greatest obstacles to the induction of anti-tumor responses. Although the selection of iPSC lines from a pre-existing bank may prove to be the most pragmatic approach to their clinical application, where appropriate lines are not available, iPSC technology offers the additional prospect of generating $CD141^+XCR1^+$ DC in a fully-autologous manner.

The invention claimed is:

1. A dendritic cell produced from a human induced pluripotent stem cell (iPSC), wherein the dendritic cell is capable of cross presenting an antigen to naïve $CD8^+T$ lymphocytes, wherein the dendritic cell expresses detectable levels of Toll-like receptor 9 (TLR9) and expresses detectable levels of XCR1, and wherein the dendritic cell lacks significant expression of the plasmacytoid dendritic cell markers CD123 and BDCA-2.

2. A dendritic cell according to claim 1, wherein the dendritic cells expresses detectable levels of TLR3 and TLR7.

3. A dendritic cell according to claim 1, wherein the dendritic cell expresses detectable levels of MHC class II.

4. A dendritic cell according to claim 1, wherein the dendritic cell is loaded or transfected with an antigen.

5. A population comprising two or more dendritic cells according to claim 1.

6. A population according to claim 5, wherein the population comprises more than $5.1 \times 10^5$ of the dendritic cells.

7. A population according to claim 5, wherein the population is autologous.

8. A population according to claim 5, wherein the population is semi-allogeneic and is optionally derived from partially matched iPSCs obtained from a public bank of clinically-approved lines.

9. A pharmaceutical composition comprising (a) a population of dendritic cells according to claim 5 and (b) a pharmaceutically acceptable carrier or diluent.

* * * * *